United States Patent [19]

Jian et al.

[11] Patent Number: 5,603,935
[45] Date of Patent: Feb. 18, 1997

[54] COMPOSITION FOR THE TREATMENT OF SNORING AND METHODS OF USE THEREOF

[75] Inventors: Weng W. Jian, Beijing, China; David S. Riley, Santa Fe, N.M.

[73] Assignee: Eastern Europe, Inc., New York, N.Y.

[21] Appl. No.: 282,961

[22] Filed: Jul. 29, 1995

(Under 37 CFR 1.47)

[51] Int. Cl.$^6$ ................................................. A61K 35/78
[52] U.S. Cl. ........................................ 424/195.1; 514/923
[58] Field of Search ....................... 424/195.1; 514/923

[56] References Cited

U.S. PATENT DOCUMENTS

| | | | |
|---|---|---|---|
| 4,064,253 | 12/1977 | Khoe | 514/356 |
| 4,324,785 | 4/1982 | Stevens | 424/195.1 |
| 4,423,030 | 12/1983 | Hayes et al. | 424/58 |
| 4,556,557 | 12/1985 | Reichert | 424/94.6 |
| 4,668,513 | 5/1987 | Reichert | 424/94.6 |
| 5,075,290 | 12/1991 | Findley et al. | 514/46 |
| 5,082,665 | 1/1992 | Verny | 424/464 |
| 5,133,964 | 7/1992 | Kim | 424/195.1 |
| 5,164,184 | 11/1992 | Kim | 424/195.1 |
| 5,190,757 | 3/1993 | Kim | 424/195.1 |
| 5,225,203 | 7/1993 | Kim | 424/195.1 |

OTHER PUBLICATIONS

Commercial Product Advertisement: "Da Tong Anti-Snoring Nostril Drop" (marketing publication).
American Institute of Homeopathy, pp. 601-602.
*HPUS 8*, vol. 1, pp. 3-20 and *HP Supp.*, pp. 36-78. General Pharmacy (1988).
Food and Drug Administration Compliance Policy Guides—Guide 7132.15, Chap. 32—Drugs—General (May 31, 1988), pp. 1-7.
Definition of *Dioscorea Villosa L.*—No. 3033 (Jun. 1991) (1 page.).
Boericke, *Homeopathic Materia with Repertory*, 9th Ed., revised 1927 (excerpt).
Hering, C., *Materia Medica* (excerpts).
Kent, J. T., *Repertory of Homeopathic Materia Medica*, Sett & Day Co., Calcutta, India, 1st Ed. 1961 (excerpts) (4 pages).
Knerr, *Repertory*, (excerpt).
Allen, T. F., *Encyclopedia* (12 volumes) (excerpt).
Boenninghausen, *Repertory* (excerpt).
Clarke, John Henry, *A Dictionary of Practical Materia Medica*, Homeopathic Publishing Co., Ltd., England, 3rd Ed. 1955 (3 vols.) (excerpt).

*Primary Examiner*—John W. Rollins
*Attorney, Agent, or Firm*—Theodore F. Shiells

[57] ABSTRACT

A composition and method for the treatment of snoring comprising an effective amount of discorea villosa and zingiber officinale in a physiologically acceptable carrier, to be administered in the form of nasal drops or spray in the nasal passages of a subject prior to sleep.

27 Claims, No Drawings

COMPOSITION FOR THE TREATMENT OF SNORING AND METHODS OF USE THEREOF

FIELD OF THE INVENTION

This invention relates to treatment for snoring, and in particular, a homeopathic treatment for snoring.

BACKGROUND OF THE INVENTION

Snoring, although not a disease, is commonly found in nearly half of the world's population. It can affect one's health and also creates great annoyance to others.

Many proposals to alleviate snoring have been proposed, including both devices and medicaments. One such proposed treatment for snoring in use in other countries is nasal drops containing an amount of dioacorea oppoaita as the sole active ingredient.

Although nasal drops incorporating dioacorea oppoaita are satisfactory in many respects for the treatment of snoring, the availability of dioacorea oppoaita for use is limited, particularly in the United States. In addition to the limited availability of dioacorea oppoaita, the effectiveness of these nasal drops is limited to the effectiveness of the single active ingredient, dioacorea oppoaita.

Homeopathic treatments are rapidly gaining in popularity and acceptance in the United States. Homeopathy relies upon the administration of small doses of substances, typically natural herbs and herb extracts. Homeopathic remedies are believed to achieve a therapeutic effect by inducing natural body mechanisms to return to their proper level of activity, characteristic of a healthful state. Homeopathic remedies function in a different manner than traditional pharmaceuticals in that they generally do not require high concentrations of active ingredients to produce the desired effects. Minute quantities of their active ingredients are often adequate to achieve the desired result. Homeopathic medicaments provides natural and relatively inexpensive alternatives to traditional remedies. Accordingly, there is a great need for a treatment for snoring using homeopathic ingredients which are widely available.

OBJECTS OF THE INVENTION

Accordingly, a primary object of the present invention is to provide a composition for the treatment of snoring which does not require dioacorea oppoaita as a primary active ingredient.

A further object of the present invention is to provide a homeopathic pharmaceutical preparation using a combination of ingredients which are widely available and effective for the treatment of snoring.

It is a still further object of the present invention to provide a method for treating snoring comprising administering to a subject an amount of a combination of herbal ingredients effective to treat snoring.

The present inventors have discovered that a nasal preparation including herbal extracts of zingiber officinale and discorea villosa as the active homeopathic ingredients provides a particularly effective snoring remedy. The inventive homeopathic remedy of the present invention does not require dioacorea oppoaita, and hence the limitations on availability of dioacorea oppoaita have been overcome. Furthermore, by combining zingiber officinale and discorea villosa together in appropriate relative concentrations, the homeopathic properties are believed to complement and augment one another, while tending to minimize the potential for undesired side effects which might be caused by either used alone. This provides a homeopathic preparation believed to have improved effectiveness.

SUMMARY OF THE INVENTION

This invention provides a composition for the treatment of snoring comprising an effective amount of discorea villosa and zingiber officinale.

Further provided by this invention is a method for treating snoring comprising nasal administration to a subject of an effective amount of discorea villosa and zingiber officinale.

DETAILED DESCRIPTION OF THE INVENTION

This invention provides a composition for the treatment of snoring comprising an effective amount of discorea villosa and zingiber officinale. In another embodiment of the invention, the composition may also include one or more herbs or herbal extracts selected from the group consisting of ammonium carbonicum, bromium, carbo animalis, pulsatilla, and dioacorea oppoaita. The invention also preferably includes a physiologically acceptable carrier. Preferably, this physiologically acceptable carrier comprises a mixture of glycerin, distilled water and alcohol. In other embodiments of the invention, the carrier further comprises sodium chloride.

In a preferred embodiment of the invention, the composition includes 5 percent by volume of a mother tincture of discorea villosa and 5 percent by volume of a mother tincture of zingiber officinale.

Most preferably the composition is in the form of a nasal spray or nasal drop.

Further provided by this invention is a method for treating snoring comprising administering to a subject an amount effective to treat snoring of discorea villosa and zingiber officinale. Preferably the method comprises administering an effective amount of discorea villosa and zingiber officinale via the nasal passage. In yet another preferred embodiment of the invention composition administered comprises 5 percent by volume of a mother tincture of discorea villosa and 5 percent by volume of a mother tincture of zingiber officinale.

Forms and shapes of vehicles for administering zingiber officinale and discorea villosa may be varied to suit taste and convenience. Tinctures, liquids, and solid attenuations may also be dispensed as suppositories, ointments, cerates, gels, or lotions for topical use. The homeopathic composition of the present invention is most preferably in the form of a nasal solution. The nasal solution is preferably isotonic and euhydric. In the present invention, sodium chloride is utilized in the preferred isotonic medium. If necessary, the nasal solution may be suitably buffered. Nasal solutions are made by the potentization of base tinctures or solutions, or by dilution with liquid. Preservatives or stabilizers may be added after the final attenuation.

Preparation of Mother Tinctures of Discorea Villosa and Zingiber Officinale:

Mother tinctures (also referred to as "tinctures" or "first solution") of crude materials are made to represent one part by weight of dry crude material in ten parts by volume of completed solution. In the present invention, discorea villosa and/or zingiber officinale are prepared by maceration or percolation from the crude substances, fresh or dried, usually with the dissolving action of an alcohol vehicle. Homeopathic tinctures can also be prepared with the addition of heat. Methods of preparing tinctures that utilize heat are known in the art and include, but are not limited to, methods such as incubation, infusion, and decoction. In the present invention, decoction is preferred.

The first solution or tincture is preferably made in the proportion of 1/10 in water or alcohol of suitable strength.

As stated, the presently claimed invention comprises discorea villosa and zingiber officinale as the active homeopathic ingredients. The preferred method of preparing the homeopathic composition of the claimed invention comprises creating a mother tincture, under decoction, of dried discorea villosa and zingiber officinale. However, several other processes for the extraction of medicinal properties from herbal substances exist and are known to homeopathic practice, and such may also be used in the present invention.

An example of the present invention is set forth below to aid in understanding the invention but in no way is meant to and should not be construed to limit the scope of the claims.

EXAMPLE

A solution of 35% distilled water by volume and 65% alcohol fortior by volume is prepared. (Alcohol fortior is 92.3 percent by weight ethyl alcohol and 7.7 percent by weight water). Discorea villosa and zingiber officinale of known moisture contents are carefully weighed. In accordance with homeopathic practice, the dry crude material is taken as the unit of strength, the tincture being made to represent one (1) part of the dry crude material in ten (10) parts of the completed solution.

Amounts of discorea villosa and zingiber officinale are added to the solution so that the amount of each (on a dried weight basis) is equal, and the total (on a dried weight basis) of both together represents one (1) part in ten (10) parts of the completed solution. Of course, the tinctures of the discorea villosa and zingiber officinale can also be prepared separately and then mixed at any time during the process with like effect.

The discorea villosa and zingiber officinale and the solution are placed into a suitable well-stoppered container and allowed to stand overnight. This mixture is heated under a reflux condenser and the boiling point maintained for 30 minutes. The alcohol content is reduced to 20% and the mixture cooled. The stoppered container with the mixture is placed in a dark room at room temperature and shaken periodically over a period of 2–4 weeks. The clear liquid is then decanted and the residue pressed out. This resulting liquid is the "mother tincture" of the discorea villosa and zingiber officinale.

It should be noted that the relative amounts of discorea villosa and zingiber officinale can vary over a considerable range, i.e., from nearly all discorea villosa to nearly all zingiber officinale. Furthermore, the alcohol content of the solution can vary over a considerable range without adverse effect. However, the proportions described above are preferred.

The mother tincture described above is mixed with glycerin, sodium chloride, and distilled water. The resultant composition preferably has the following formula:

5% discorea villosa mother tincture
5% zingiber officinale mother tincture
10% glycerin
0.7% sodium chloride
77.3% distilled water
2.0% alcohol The alcohol and a portion of the distilled water of the completed composition of the present invention are from the mother tincture of the discorea villosa and zingiber officinale.

Of course, the relative proportions of the glycerin, sodium chloride, distilled water and alcohol can be varied over a wide range. For example, the glycerine may be as low as 5%, the alcohol as high as 5%, and the distilled water as high as 80%.

The composition of the present invention is preferably administered in the form of nasal drops or a nasal spray. For best results, approximately two drops are administered into each nostril before sleep.

Discorea villosa and zingiber officinale are not the only substances which can be used in the present invention. In addition to these, or in lieu thereof, the composition of the present invention may also include one or more herbs or herbal extracts selected from the group consisting of ammonium carbonicum, bromium, carbo animalis, and/or pulsatilla. Dioacorea oppoaita can also be used, if available. However, although the relative proportion of the individual ingredients may vary, the total strength of the ingredients to the total composition (including the water, alcohol, sodium chloride and glycerine) is preferably in the range of 10% of the total composition.

Although the present invention has been described in accordance with a preferred embodiment thereof, it will be seen by those skilled in the art that many modifications can be made without departing from the scope and spirit of the present invention, and there is no intention in limiting the present invention to only the preferred embodiment.

What is claimed is:

1. A composition for the treatment of snoring comprising a combination of approximately equal proportions of attenuations of discorea villosa and zingiber officinale, the combination representing approximately 10% by volume of the total volume of the composition.

2. The composition of claim 1, wherein the composition further comprises one or more herbs or herbal extracts selected from the group consisting of ammonium carbonicum, bromium, carbo animalis pulsatilla, and dioacorea oppoaita.

3. The composition of claim 1, wherein the composition further comprises a physiologically acceptable carrier.

4. The composition of claim 3, wherein the physiologically acceptable carrier comprises a mixture of glycerin, distilled water and alcohol.

5. The composition of claim 4, wherein the physiologically acceptable carrier further comprises sodium chloride.

6. The composition of claim 1, wherein the amount of discorea villosa is about 5% by volume of the total composition.

7. The composition of claim 1, wherein the amount of zingiber officinale is about 5% by volume of the total composition.

8. The composition of claim 1, wherein the composition is a nasal spray.

9. The composition of claim 1, wherein the composition is a nasal drop.

10. A composition for the treatment of snoring comprising approximately equal proportions of two or more attenuations taken from the group of attenuations of discorea villosa, zingiber officinale, ammonium carbonicum, bromium, and carbo animalis pulsatilla, in an amount accounting for approximately 10% by volume of the total volume of the composition.

11. The composition of claim 10, wherein the composition further comprises a physiologically acceptable carrier.

12. The composition of claim 11, wherein the physiologically acceptable carrier comprises a mixture of glycerin, distilled water and alcohol.

13. The composition of claim 12, wherein the physiologically acceptable carrier further comprises sodium chloride.

14. A method for treating snoring comprising the step of administering to a person in need thereof an effective amount of a composition comprising approximately equal proportions of attenuations of discorea villosa and zingiber officinale.

15. The method of claim 14, wherein administration is via the nasal passage.

16. The method of claim 15, wherein the composition is administered in the form of a nasal spray.

17. The method of claim 15, wherein the composition is administered in the form of nasal drops.

18. The method of claim 14, wherein the amount of discorea villosa is about 5% by volume of the total volume of the combination.

19. The method of claim 14, wherein the amount of zingiber officinale is about 5% by volume of the total volume of the combination.

20. The method of claim 14, wherein said composition further comprises one or more herbs or herbal extracts selected from the group consisting of ammonium carbonicum, bromium, carbo animalis pulsatilla and dioacorea oppoaita.

21. The method of claim 14, wherein the composition further comprises a physiologically acceptable carrier.

22. The method of claim 21, wherein the physiologically acceptable carrier comprises a mixture of glycerin, distilled water and alcohol.

23. The method of claim 22, wherein the physiologically acceptable carrier further comprises sodium chloride.

24. A method for the treatment of snoring in a person in need thereof comprising the step of administering an effective amount of a composition including two or more attenuations taken from the group of attenuations of discorea villosa, zingiber officinale, ammonium carbonicum, bromium, and carbo animalis pulsitilla, in approximately equal proportions, in a total amount representing approximately 10% by volume of the total volume of the composition.

25. The method of claim 24, wherein the composition further comprises a physiologically acceptable carrier.

26. The method of claim 25 wherein the physiologically acceptable carrier comprises a mixture of glycerin, distilled water and alcohol.

27. The method of claim 26, wherein the physiologically acceptable carrier further comprises sodium chloride.

* * * * *

UNITED STATES PATENT AND TRADEMARK OFFICE
CERTIFICATE OF CORRECTION

PATENT NO. : 5,603,935
DATED : February 18, 1997
INVENTOR(S) : Weng W. Jian and David S. Riley It is certified that error appears in the above-indentified patent and that said Letters Patent is hereby corrected as shown below:

The filing date "Jul. 29, 1995" is corrected to -- Jul. 29, 1994 --.

Signed and Sealed this

Twenty-second Day of April, 1997

Attest:

BRUCE LEHMAN

*Commissioner of Patents and Trademarks*

*Attesting Officer*